US006410725B1

(12) United States Patent
Scholl et al.

(10) Patent No.: US 6,410,725 B1
(45) Date of Patent: Jun. 25, 2002

(54) METHOD FOR EXTRACTING DNA FROM DRIED SPECIMENS

(75) Inventors: Thomas Scholl, Salt Lake City; Michael T. Pyne, Midvale, both of UT (US); Arnold R Oliphant, Poway, CA (US)

(73) Assignee: Myriad Genetics Inc., Salt Lake City, UT (US)

( * ) Notice: Subject to any disclaimer, the term of this patent is extended or adjusted under 35 U.S.C. 154(b) by 0 days.

(21) Appl. No.: 09/513,179

(22) Filed: Feb. 25, 2000

Related U.S. Application Data

(60) Provisional application No. 60/122,113, filed on Feb. 26, 1999.

(51) Int. Cl.$^7$ ............................................... C07H 21/04
(52) U.S. Cl. .................................. 536/25.42; 536/25.41
(58) Field of Search .......................... 536/25.41, 25.42

(56) References Cited

U.S. PATENT DOCUMENTS

| | | | | |
|---|---|---|---|---|
| 4,348,478 A | * | 9/1982 | Nakano et al. | |
| 4,752,565 A | * | 6/1988 | Folks et al. | |
| 4,762,780 A | * | 8/1988 | Spector et al. | |
| 5,063,162 A | * | 11/1991 | Kiefer | 435/270 |
| 5,231,015 A | | 7/1993 | Cummins et al. | 435/91 |
| 5,234,809 A | | 8/1993 | Boom et al. | 435/91 |
| 5,334,499 A | | 8/1994 | Burdick et al. | 435/6 |
| 5,348,855 A | * | 9/1994 | Dattagupta et al. | 435/6 |
| 5,407,823 A | * | 4/1995 | Sokoloff et al. | |
| 5,496,562 A | * | 3/1996 | Burgoyne | 424/488 |
| 5,596,092 A | | 1/1997 | Schneider | 536/25.4 |
| 5,631,132 A | | 5/1997 | Lott et al. | 435/6 |
| 5,807,527 A | | 9/1998 | Burgoyne et al. | 422/488 |
| 5,830,759 A | * | 11/1998 | Chang et al. | |
| 5,861,253 A | * | 1/1999 | Asgari et al. | |
| 6,043,032 A | * | 3/2000 | Yamagishi et al. | |

FOREIGN PATENT DOCUMENTS

| WO | 0357437 A2 | * | 3/1989 |
| WO | 9641810 | | 12/1996 |

OTHER PUBLICATIONS

Brown, 1993. in Ausubel et al., eds. Current Protocols in Molecular Biology. John Wiley and Sons, Inc. pp. 2.10.1–2.10.16.*

Neugebauer, 1990. Detergents: an Overview. in Deutscher, ed. Methods in Enzymology, vol. 182. Guide to Protein Purification. Academic Press, Inc. pp. 239, 247 (Table III), 253, 254.*

Stoll et al., 1990. Buffers: Principles and Practice. in Deutscher, ed. Methods in Enzymology, vol. 182. Guide to Protein Purification. Academic Press, Inc. pp. 24, 26,27,28.*

Sambrook et al. 1989. Molecular Cloning a Laboratory Manual. Cold Spring Harbor Laboratory Press. pp. 9.14, 9.16–9.21.*

Innis et al. 1990. Optimization of PCRs. in Innis et al. PCR Protocols, a guide to methods and applications. Academic Press, Inc. pp. 3–7.*

Gelfand et al. 1990. Thermostable DNA Polymerases. in Innis et al. PCR Protocols, a guide to methods and applications. Academic Press, Inc. pp. 129, 136, 137, 138.*

Gong et al. (1994). "A selective procedure for DNA extraction from apoptotic cells applicable for gel electrophoresis and flow cytometry." *Anal. Biochem.* 218:314–319.

Pierce Immunotechnology Catalog & Handbook, pp. F2–F3 (1992).

Carducci, C. et al. "DNA Elution and Amplification by Polymerase Chain Reaction from Dried Blood Spots", Bio-Techniques, 1992; vol. 13:5, 735–737.

McCabe, E. et al. "DNA Microextraction from dried blood spots on filter paper blotters: potential applications to newborn screening", Human Genetics; 1987, 213–216.

Singh, B. et al. "Detection of malaria in Malaysia by nested polymerase chain reaction amplification of dried blood spots on filter papers", Transactions of the Royal Society of Tropical Medicine and Hygiene; 1996;90:519–521.

Makowski, G.S. et al. "Polymerase Chain Reaction Amplification of Gguthrie Card Deoxyribonucleic Acid: Extraction of nucleic Acid from Filter Matrices", Annals of Clinical and Laboratory Sciences; 1998 vol. 38 No. 4:254–259.

Noda, S. et al. "Detection of human T–cell lymphotropic virus type 1 infection by the polymerase chain reaction using dried blood specimens on filter paper"; Journal of Virological Methods; 1993, 43:111–122.

Berlin, Y. et al. "Rapid Preparation of Genomic DNA Form Dried Blood and Saliva Spots for Polymerase Chain Reaction"; Human Mutation; 1992; 1:260–261.

Gentra Systems, Inc. "Generation Capture Card Kit"; Product Pamphlet; 1998.

Fitczo Inc. "FTA: Procedure For RFLP Analysis From Blood Spotted on FTA Paper", Product Pamphlet.

DeVange Panteleeff, D. et al. "Rapid Method for Screening Dried Blood Samples on Filter Paper for Human Immunodeficiency Virus Type 1 DNA", Journal of Clinical Microbiology; 1999 p. 350–353, 37:2.

* cited by examiner

*Primary Examiner*—Remy Yucel
*Assistant Examiner*—Bronwen M. Loeb
(74) *Attorney, Agent, or Firm*—Rothwell, Figg, Ernst & Manbeck p.c.

(57) ABSTRACT

The present invention relates to a composition and to a method for extracting DNA. More specifically, the present invention relates to a composition and to a method to extract DNA from dried biological samples on solid substrates, including but not limited to, buccal smears, semen and especially blood. The method can be conducted in a single-tube. The DNA extracted in accordance with the present invention can be used for DNA amplification reactions, DNA sequencing, DNA restriction analysis and DNA hyridization.

19 Claims, No Drawings

METHOD FOR EXTRACTING DNA FROM DRIED SPECIMENS

CROSS-REFERENCE TO RELATED APPLICATION

The present application is related to U.S. provisional patent application Ser. No. 60/122,113 filed on Feb. 26, 1999, incorporated herein by reference.

BACKGROUND OF THE INVENTION

The present invention relates to a composition and to a method for extracting DNA. More specifically, the present invention relates to a composition and to a method to extract DNA from dried biological samples on solid substrates, including but not limited to, buccal smears, semen and especially blood. The method can be conducted in a single-tube. The DNA extracted in accordance with the present invention can be used for DNA amplification reactions, DNA sequencing, DNA restriction analysis and DNA hyridization.

Blood and other biological samples are commonly archived by applying the sample to filter paper and allowing it to dry. These samples are used for newborn screening, diagnostic testing, and felon databasing. Samples are typically applied to filter paper cards and allowed to dry. Two types of filter paper cards are prevalent, Schleicher & Schuell 903 (S&S 903) and Fitzco FTA™ cards. S&S 903 paper is a heavy, highly absorbent cotton bond paper. Fitzco FTA™ cards are similar, but are treated with several compounds (U.S. Pat. No. 5,496,562) designed to kill pathogens and resist bacterial growth and DNA degradation. These compounds include Tris, EDTA, SDS, and uric acid. Fitzco claims that the "membranes are disrupted and the DNA explodes out of the nucleus causing high molecular weight DNA to become entangled in the fibers of the paper" (Fitzco Product Information).

To perform molecular diagnostic studies such as polymerase chain reaction (PCR) and restriction fragment length polymorphism (RFLP), the DNA must be purified in situ or extracted from the paper matrix. The currently available protocols require lengthy enzymatic digestions, incubations, and separation steps. Many of these protocols produce very little, poor quality DNA and are not amenable to high-throughput applications. Furthermore, protocols for FTA paper recommend amplification directly from the paper, since it is reported that it is difficult to get the DNA into solution.

There are several drawbacks to this last approach. There is no method to measure the amount or purity of DNA available in the paper. The protocol for RFLP requires enzymatic digestion to release the DNA from the paper matrix. Since the RFLP protocol involves enzymatic digestion, it poses the problems mentioned above.

Paper punchers are available, but this process is difficult to automate reliably. Static electricity and normal air movements can cause mishandling of the paper punches. Finally, the smallest available punchers are 1 mm in diameter, which does not fit in a 384-well microtiter plate. This places a lower limit on PCR reactions, which can increase the consumption of expensive reagents.

Therefore, it is desirable to develop a simple, rapid, high-throughput method to release the DNA from the paper matrix and a composition to be used in this method. DNA in solution is more easily applied to automated processes.

SUMMARY OF THE INVENTION

The present invention relates to a composition and to a method for extracting DNA. More specifically, the present invention relates to a composition and to a method to extract DNA from biological samples, especially blood dried on cellulosic material, such as paper. The method can be conducted in a single-tube. The DNA extracted in accordance with the present invention can be used for DNA amplification reactions, DNA sequencing, DNA restriction analysis and DNA hybridization.

In accordance with one embodiment of the present invention, a DNA extraction composition (solution) is provided which comprises formamide, citrate, a suitable buffer and optionally a non-ionic detergent. In accordance with a second embodiment of the present invention, a method for extracting DNA from biological samples is provided. In one aspect of the invention, the biological sample is blood. In a second aspect of the invention, the blood is dried on a cellulosic material. The method comprises contacting the biological sample with the DNA extraction solution, heating the resultant mixture and isolating supernatant containing the extracted DNA. This method is suitable for extracting DNA in a single tube.

DETAILED DESCRIPTION OF THE INVENTION

Current procedures for extracting DNA from certain biological samples, such as dried blood on cellulosic material such as cotton based papers (e.g., Schleicher & Schuell 903 (S&S 903) and Fitzco FTA™ cards), require lengthy enzymatic digestions, incubations and separation steps. In addition, compounds used as preservatives in FTA™ paper would become soluble as a result of DNA extraction or DNA amplification reactions and inhibit enzymes.,used for DNA amplification. Thus, it was desired to develop a simple, rapid, high-throughput method to release the DNA from the paper matrix. It was further desired to develop a composition to be used in this method which would not only serve to extract the DNA, but would also serve to remove or inactivate the compounds present in FTA™ paper. The method and composition described herein satisfies these desires and produces DNA that is suitable for use in molecular procedures, including amplification, sequencing, hybridization and restriction analysis.

In accordance with one aspect of the present invention, a composition is provided which is capable of (i) extracting DNA from a biological sample, such as buccal smears, semen and particularly blood, dried on a cellulosic material, such as cotton based papers and (ii) removing or inactivating compounds present in the cellulosic material that may otherwise interfere in analysis of the DNA. The DNA composition of the present invention is further capable of extracting sufficient DNA for molecular analysis in a single tube in a simple method. According to the present invention, the DNA extraction composition comprises (1) formamide, (2) citrate and (3) a buffer. The DNA extraction composition may optionally comprises a non-ionic detergent.

The DNA composition comprises formamide in an amount from about 5% to about 90%, preferably from about 5% to about 50%, and more preferably about 10%. The DNA extraction composition comprises citrate in an amount from about 5 mM to about 60 mM, preferably from about 10 mM to about 40 mM, and more preferably about 20 mM. The DNA extraction composition comprises a buffer in the amount from about 1 mM to about 300 mM, preferably from about 10 mM to about 150 mM, more preferably about 50 mM. The pH of the buffer is from about 6.0 to about 8.8, preferably from about 7.5 to about 8.3, and more preferably about 7.8. Non-limiting examples of the buffer include acetate, BES, citrate, glycine, HEPES, MES, phosphate, PIPES, Tricine and Tris. It is preferred to use Tris. The DNA extraction composition may optionally comprise a non-ionic detergent from about 0.1% to about 50%, preferably from about 0.5% to about 10%, and more preferably about 1%. Non-limiting examples of non-ionic detergent include Nonidet NP-40, Triton® X-100 (octoxynol), Tween® 20 (polyoxyethylenesorbitan monolaurate) and Tween® 80 (polyoxyethylenesorbitan monooleate). It is preferred to use Tween® 80.

In accordance with a second aspect of the present invention, a simple, rapid, highthroughput method is provided to release DNA from a biological sample, especially from a biological sample adsorbed to a cellulosic material, such as cotton based papers. The method can be performed in a single tube, thus greatly simplifying the DNA extraction process for biological samples, especially blood, dried on cotton based papers. According to the present invention, the DNA extraction method comprises (a) contacting a biological sample with the DNA extraction composition described above, (b) incubating the mixture at a low temperature, (c) incubating the mixture at an elevated temperature and (d) isolating the supernatant which contains the solubilized, extracted DNA.

A disk of cellulosic material containing a biological material is added to a tube or a well, such as a microtiter well. Any mass of substrate can be immersed in this composition for DNA extraction. Commercial paper punches are available that produce sizes useful for 96-well format plates (1–5 mm). The process of the present invention performs well with a variety of punch sizes and with various numbers of punches extracted as a single sample. These conditions include sizes of the disks is in the range from about I mm to about 5 mm, with between 1 and 20 punches per well. The DNA extraction composition described herein is added to the tube or well containing the disk(s) in an amount from about 20 µL to about 300 µL, preferably from about 40 µL to about 100 µL, and more preferably about 50 µL. The disk(s) and DNA extraction solution is first incubated for about 0.5 minutes to about 60 minutes, preferably for about 5 minutes to about 20 minutes, and more preferably for about 10 minutes at a temperature of from about 40° C. to about 60° C., preferably from about 10° C. to about 45° C., and more preferably at room temperature (25° C.). The disk(s) and DNA extraction solution is then incubated for about 0.5 minutes to about 60 minutes, preferably for about 5 minutes to about 20 minutes, and more preferably for about 10 minutes at an elevated temperature of from about 45° C. to about 100° C., preferably from about 55° C. to about 100° C., and more preferably at 95° C. The supernatant is then isolated using any suitable technique. One suitable technique is centrifugation, such as 3000 × g for 10 minutes. The supernatant can then be used in molecular techniques such as amplification reactions, hybridization analysis, sequencing and restriction analysis. It has been found that the supernatant can be used as target for amplification reactions following a dilution of 5–10 fold, preferably 8-fold, at a 10% to 20% final reaction volume.

EXAMPLES

The present invention is further detailed in the following Examples, which are offered by way of illustration and are not intended to limit the invention in any manner. Standard techniques well known in the art or the techniques specifically described below are utilized.

Example 1

Materials and Methods

Blood samples and paper cards:

The samples used in this procedure consisted either of EDTA-anticoagulated whole venous blood or capillary blood collected by standard procedures. The blood was applied to either S&S 903 or FTA™ blood collection cards and dried at room temperature. The dried cards were stored in the dark in plastic bags at room temperature.

PCR Amplification:

PCR reactions were carried out in 384-well microtiter plates in 10 µL volumes using Amplitaq Gold (Perkin Elmer) and primers that amplify an approximately 560 bp region of Exon 11 of the BRCAl tumor-suppressor gene. Targets are described below and also included positive and negative controls.

Agarose gel electrophoresis:

PCR products were electrophoresed on 1% SeaKem GTG (FMC) agarose with 100 bp ladder or λ HindIII fragment size standards. The gels were stained with ethidium bromide and photographed using a Kodak MP4+ Polaroid camera system.

Example 2

Identifying Reagent Candidates

Since components of blood (hemoglobin) and FTA™ paper (SDS) are known to inhibit PCR amplification we sought to identify reagents that could reverse the inhibition of PCR by hemoglobin and SDS. First, we established concentrations of these compounds compatible with PCR amplification.

The compounds and concentrations tested in the PCR reactions are listed in Table 1. These PCR reactions used 20 ng genomic DNA as a target. The FTA supernatant was prepared by incubating eight 3 mm bloodstained FTA™ disks in 500 µL of water for 20 minutes, centrifuging briefly, and collecting the supernatant. FTA supernatant and SDS both proved to be potent inhibitors of PCR. The candidate compounds for inhibition reversal have been titrated to determine upper thresholds for their concentrations in PCR reactions. Those concentrations, shown in Table 1, that do not adversely affect PCR were further tested for their ability to reverse PCR inhibition.

TABLE 1

Titration of Compounds in PCR

| | FTA Supernatant % | SDS % | Betaine mM | BSA mg/ml | Acetyl BSA mg/ml | DMSO % | EDTA mM | Formamide % | Gelatin mg/ml |
|---|---|---|---|---|---|---|---|---|---|
| 1 | 50.0000 | 5.0000 | 2.5000 | 10.0000 | 0.5000 | 50.0000 | 20.0000 | 50.0000 | 10.0000 |
| 2 | 25.0000 | 2.5000 | 1.2500 | 5.0000 | 0.2500 | 25.0000 | 10.0000 | 25.0000 | 5.0000 |
| 3 | 12.5000 | 1.2500 | 0.6250 | 2.5000 | 0.1250 | 12.5000 | 5.0000 | 12.5000 | 2.5000 |
| 4 | 6.2500 | 0.6250 | 0.3125 | 1.2500 | 0.0625 | 6.2500 | 2.5000 | 6.2500 | 1.2500 |
| 5 | 3.1250 | 0.3125 | 0.1563 | 0.6250 | 0.0313 | 3.1250 | 1.2500 | 3.1250 | 0.6250 |
| 6 | 1.5625 | 0.1563 | 0.0781 | 0.3125 | 0.0156 | 1.5625 | 0.6250 | 1.5625 | 0.3125 |
| 7 | 0.7813 | 0.0781 | 0.0391 | 0.1563 | 0.0078 | 0.7813 | 0.3125 | 0.7813 | 0.1563 |
| 8 | 0.3906 | 0.0391 | 0.0195 | 0.0781 | 0.0039 | 0.3906 | 0.1563 | 0.3906 | 0.0781 |
| 9 | 0.1953 | 0.0195 | 0.0098 | 0.0391 | 0.0020 | 0.1953 | 0.0781 | 0.1953 | 0.0391 |
| 10 | 0.0977 | 0.0098 | 0.0049 | 0.0195 | 0.0010 | 0.0977 | 0.0391 | 0.0977 | 0.0195 |
| 11 | 0.0488 | 0.0049 | 0.0024 | 0.0098 | 0.0005 | 0.0488 | 0.0195 | 0.0488 | 0.0098 |
| 12 | 0.0244 | 0.0024 | 0.0012 | 0.0049 | 0.0002 | 0.0244 | 0.0098 | 0.0244 | 0.0049 |
| 13 | 0.0122 | 0.0012 | 0.0006 | 0.0024 | 0.0001 | 0.0122 | 0.0049 | 0.0122 | 0.0024 |
| 14 | 0.0061 | 0.0006 | 0.0003 | 0.0012 | 0.0001 | 0.0061 | 0.0024 | 0.0061 | 0.0012 |
| 15 | 0.0031 | 0.0003 | 0.0002 | 0.0006 | 0.0000 | 0.0031 | 0.0012 | 0.0031 | 0.0006 |

| | Glycerol % | Histidine mM | NP-40 % | PEG 8000 % | Tricine pH 7.8 mM | Triton ® X-100 % | Tween ® 20 % | Tween ® 80 % |
|---|---|---|---|---|---|---|---|---|
| 1 | 20.0000 | 25.0000 | 20.0000 | 20.0000 | 250.0000 | 10.0000 | 20.0000 | 10.0000 |
| 2 | 10.0000 | 12.5000 | 10.0000 | 10.0000 | 125.0000 | 5.0000 | 10.0000 | 5.0000 |
| 3 | 5.0000 | 6.2500 | 5.0000 | 5.0000 | 62.5000 | 2.5000 | 5.0000 | 2.5000 |
| 4 | 2.5000 | 3.1250 | 2.5000 | 2.5000 | 31.2500 | 1.2500 | 2.5000 | 1.2500 |
| 5 | 1.2500 | 1.5625 | 1.2500 | 1.2500 | 15.6250 | 0.6250 | 1.2500 | 0.6250 |
| 6 | 0.6250 | 0.7813 | 0.6250 | 0.6250 | 7.8125 | 0.3125 | 0.6250 | 0.3125 |
| 7 | 0.3125 | 0.3906 | 0.3125 | 0.3125 | 3.9063 | 0.1563 | 0.3125 | 0.1563 |
| 8 | 0.1563 | 0.1953 | 0.1563 | 0.1563 | 1.9531 | 0.0781 | 0.1563 | 0.0781 |
| 9 | 0.0781 | 0.0977 | 0.0781 | 0.0781 | 0.9766 | 0.0391 | 0.0781 | 0.0391 |
| 10 | 0.0391 | 0.0488 | 0.0391 | 0.0391 | 0.4883 | 0.0195 | 0.0391 | 0.0195 |
| 11 | 0.0195 | 0.0244 | 0.0195 | 0.0195 | 0.2441 | 0.0098 | 0.0195 | 0.0098 |
| 12 | 0.0098 | 0.0122 | 0.0098 | 0.0098 | 0.1221 | 0.0049 | 0.0098 | 0.0049 |
| 13 | 0.0049 | 0.0061 | 0.0049 | 0.0049 | 0.0610 | 0.0024 | 0.0049 | 0.0024 |
| 14 | 0.0024 | 0.0031 | 0.0024 | 0.0024 | 0.0305 | 0.0012 | 0.0024 | 0.0012 |
| 15 | 0.0012 | 0.0015 | 0.0012 | 0.0012 | 0.0153 | 0.0006 | 0.0012 | 0.0006 |

Key:
No PCR product detected
Reduced PCR product detected
Concentrations of reagents selected for further inhibition experiments

Example 3

Testing PCR Inhibition by Hemoglobin and SDS

The purpose of the next experiment was to test PCR inhibition by hemoglobin and SDS separately. S&S 903 supernatant was prepared by incubating 8–3 mm blood-stained S&S 903 disks in 500 µL water for 5 minutes at 95° C., centrifuging briefly, and collecting the supernatant. This supernatant and SDS were tested as above for inhibition of PCR. Two-fold serial dilutions indicated that 0.1% SDS completely inhibited PCR, while 50–12.5% S&S 903 supernatant partially inhibited PCR. SDS concentrations of 0.02, 0.01 and 0.005% and S&S 903 supernatant concentrations of 25, 12.5, and 6.25% were chosen as the concentrations in PCR to test reversal of inhibition. These three concentrations of inhibitors were each tested against three concentrations of reagent that might reverse inhibition. Table 2 details the results of this experiment. All of the nonionic detergents were capable of reversing SDS inhibition to some extent. The S&S 903 supernatant seemed to extract insufficient material to inhibit PCR.

TABLE 2

Reversal of PCR Inhibition

| 903 Supernatant | 25% | | | 12.5% | | | 6.25% | | |
|---|---|---|---|---|---|---|---|---|---|
| Betaine (mM) | 312.00 | 156.00 | 78.00 | 312.00 | 156.00 | 78.00 | 312.00 | 156.00 | 78.00 |
| BSA (mg/ml) | 1.25 | 0.63 | 0.31 | 1.25 | 0.63 | 0.31 | 1.25 | 0.63 | 0.31 |
| Acetyl-BSA (mg/ml) | 0.25 | 0.13 | 0.06 | 0.25 | 0.13 | 0.06 | 0.25 | 0.13 | 0.06 |
| DMSO (%) | 5.00 | 2.50 | 1.25 | 5.00 | 2.50 | 1.25 | 5.00 | 2.50 | 1.25 |
| EDTA (mM) | 0.63 | 0.31 | 0.16 | 0.63 | 0.31 | 0.16 | 0.63 | 0.31 | 0.16 |
| Formamide (%) | 0.20 | 0.10 | 0.05 | 0.20 | 0.10 | 0.05 | 0.20 | 0.10 | 0.05 |
| Gelatin (%) | 0.04 | 0.02 | 0.00 | 0.04 | 0.02 | 0.00 | 0.04 | 0.02 | 0.00 |
| Glycerol (%) | 2.50 | 1.25 | 0.63 | 2.50 | 1.25 | 0.63 | 2.50 | 1.25 | 0.63 |

TABLE 2-continued

Reversal of PCR Inhibition

| | | | | | | | | | |
|---|---|---|---|---|---|---|---|---|---|
| Histidine (mM) | 0.25 | 0.13 | *0.06* | 0.25 | 0.13 | *0.06* | 0.25 | 0.13 | 0.06 |
| NP-40 (%) | *2.50* | *1.25* | *0.63* | 2.50 | *1.25* | 0.63 | 2.50 | 1.25 | 0.63 |
| PEG (%) | 1.25 | 0.63 | 0.31 | 1.25 | 0.63 | 0.31 | 1.25 | 0.63 | 0.31 |
| Tricine (mM) | 2.50 | 1.25 | 0.63 | 2.50 | 1.25 | 0.63 | 2.50 | 1.25 | 0.63 |
| Triton ® X-100 (%) | 2.50 | *1.25* | *0.63* | 2.50 | *1.25* | *0.63* | 2.50 | *1.25* | *0.63* |
| Tween ® 20 (%) | 2.50 | 1.25 | 0.63 | 2.50 | 1.25 | 0.63 | 2.50 | 1.25 | 0.63 |
| Tween ® 80 (%) | 2.50 | 1.25 | 0.63 | 2.50 | 1.25 | 0.63 | 2.50 | 1.25 | 0.63 |
| SDS | | 0.02% | | | 0.01% | | | 0.005% | |
| Betaine (mM) | 312.00 | 156.00 | 78.00 | 312.00 | 156.00 | 78.00 | 312.00 | 156.00 | 78.00 |
| BSA (mg/ml) | 1.25 | 0.63 | 0.31 | 1.25 | 0.63 | 0.31 | 1.25 | 0.63 | 0.31 |
| Acetyl-BSA (mg/ml) | 0.25 | 0.13 | 0.06 | 0.25 | 0.13 | 0.06 | 0.25 | 0.13 | 0.06 |
| DMSO (%) | 5.00 | 2.50 | 1.25 | 5.00 | 2.50 | 1.25 | 5.00 | 2.50 | 1.25 |
| EDTA (mM) | 0.63 | 0.31 | 0.16 | 0.63 | 0.31 | 0.16 | 0.63 | 0.31 | 0.16 |
| Formamide (%) | 0.20 | 0.10 | 0.05 | 0.20 | 0.10 | 0.05 | *0.20* | 0.10 | 0.05 |
| Gelatin (%) | 0.04 | 0.02 | 0.00 | 0.04 | 0.02 | 0.00 | 0.04 | *0.02* | *0.00* |
| Glycerol (%) | 2.50 | 1.25 | 0.63 | 2.50 | 1.25 | 0.63 | *2.50* | 1.25 | *0.63* |
| Histidine (mM) | 0.25 | 0.13 | 0.06 | 0.25 | 0.13 | 0.06 | *0.25* | 0.13 | 0.06 |
| NP-40 (%) | <u>2.50</u> | <u>1.25</u> | 0.63 | <u>2.50</u> | <u>1.25</u> | <u>0.63</u> | 2.50 | 1.25 | 0.63 |
| PEG (%) | 1.25 | 0.63 | 0.31 | 1.25 | 0.63 | 0.31 | 1.25 | 0.63 | 0.31 |
| Tricine (mM) | 2.50 | 1.25 | 0.63 | 2.50 | 1.25 | 0.63 | *2.50* | *1.25* | 0.63 |
| Triton ® X-100 (%) | <u>2.50</u> | <u>1.25</u> | 0.63 | <u>2.50</u> | <u>1.25</u> | <u>0.63</u> | 2.50 | 1.25 | 0.63 |
| Tween ® 20 (%) | <u>2.50</u> | <u>1.25</u> | 0.63 | <u>2.50</u> | <u>1.25</u> | <u>0.63</u> | 2.50 | 1.25 | 0.63 |
| Tween ® 80 (%) | <u>2.50</u> | <u>1.25</u> | <u>0.63</u> | <u>2.50</u> | <u>1.25</u> | <u>0.63</u> | 2.50 | 1.25 | 0.63 |

Key:
Strong PCR Inhibition
*Moderate PCR Inhibition*
<u>Moderate Reversal of PCR Inhibition</u>
<u>Strong Reversal of PCR Inhibition</u>

Example 4

Increasing, Solubility of Extracted Material

In an attempt to increase the amount of material extracted from S&S 903 paper, the incubation time was increased and formamide was included in the composition. The objective was to test the ability of a formamide solution could extract more material from the blood spots and increase its solubility. Eight 3 mm bloodstained S&S 903 disks in 500 μL of water or 95% formamide in 100 mM Tris pH 8.3 at room temperature for 10 minutes. The disks were then incubated for 10 minutes at 95° C. The solutions were centrifuged and the supernatants collected. While the samples extracted with water produced large pellets of insoluble material, the samples extracted with formamide remained soluble.

These supernatants were tested for inhibition of PCR and for the presence of DNA. Each supernatant was tested in a two-fold dilution series starting at 25% supernatant in the standard PCR reaction. Each supernatant was also tested for DNA in a two-fold dilution series starting at 20% concentration as a target in PCR. The results are shown in Table 3.

The longer incubation seems to extract more material from the disks. The extraction with formamide produced almost no insoluble material and was a better target for PCR. Formamide extraction looks promising, although it is inhibitory at higher concentrations.

TABLE 3

Formamide Versus Water Extraction

| Inhibition | | Test for DNA | |
|---|---|---|---|
| Formamide % | Water % | Formamide % | Water % |
| 25.0000 | 25.0000 | 20.0000 | 20.0000 |
| 12.5000 | 12.5000 | 10.0000 | 10.0000 |
| 6.2500 | 6.2500 | 5.0000 | 5.0000 |
| 3.1250 | 3.1250 | 2.5000 | 2.5000 |
| 1.5625 | 1.5625 | 1.2500 | 1.2500 |
| 0.7813 | 0.7813 | 0.6250 | 0.6250 |
| 0.3906 | 0.3906 | 0.3125 | 0.3125 |
| 0.1953 | 0.1953 | 0.1563 | 0.1563 |
| 0.0977 | 0.0977 | 0.0781 | 0.0781 |
| 0.0488 | 0.0488 | 0.0391 | 0.0391 |
| 0.0244 | 0.0244 | 0.0195 | 0.0195 |
| 0.0122 | 0.0122 | 0.0098 | 0.0098 |
| 0.0061 | 0.0061 | 0.0049 | 0.0049 |
| 0.0031 | 0.0031 | 0.0024 | 0.0024 |
| 0.0015 | 0.0015 | 0.0012 | 0.0012 |

Key: No PCR Product
Little PCR Product
Moderate PCR Product
Good PCR Product

Example 5

Optimizing Formamide Concentration in Extraction

Next, extractions were performed in reduced volumes and with reduced concentrations of formamide in an attempt to improve the formamide to DNA ratio while keeping the extracted material soluble. Eight 3 mm bloodstained S&S 903 disks were extracted in 500 or 100 μL volumes of 95% formamide in 100 mM Tris pH 8.3, water, or a 1:1 mixture of water and the 95% formamide/100 mM Tris solution as described earlier. These solutions were used in two-fold dilution series ($2^0$ through $2^{-12}$) as targets in PCR (2 μL in 10 μL reaction). Genomic DNA and no target controls were also performed. Amplification was detected in samples extracted with 100 μL 1:1 formamide solution:water for dilutions $2^{-4}$ through $2^{-7}$ and from those extracted with 500 μL water for dilutions $2^0$ and $2^{-1}$. This is the first successful amplification from DNA extracted by a one-step process.

Example 6

Testing Alternatives to Formamide

The PCR reaction may be improved by identifying alternatives to formamide which solubilize material, but are less inhibitory, or using decreased concentrations of formamide.

The inhibitory effects of twelve reagents as alternatives to formamide were tested in PCR. The amplification was scored for performance by (1) failure-no detectable PCR product, (2) compromised-less PCR product compared to controls, or (3) nominal-PCR product similar to controls. The reagents and the concentrations in PCR that fit these scores are listed in Table 4. Overall, the glycols were less inhibitory to PCR than the amines. Inhibition by the amines was similar to that of formamide. Glycols can now be tested in the DNA extraction solution.

TABLE 4

Testing Alternatives to Formamide

| Reagent | PCR Performance (reagent % in PCR) | | |
|---|---|---|---|
|  | Failed | Compromised | Nominal |
| 4-Acetylmorpholine | 10 | 5 | 2.5 |
| 1,4-Butanediol | 10 | — | 5 |
| Diethylene Glycol | 20 | — | 10 |
| 1,3-Dimethyl-s-Imidazolidinone | 5 | — | 2.5 |
| Dipropylene Glycol | 20 | 10 | 5 |
| 3-Hydroxypropionitrile | 10 | — | 5 |
| 1-Methyl-2-Pyrrolidinone | 10 | 5 | 2.5 |
| 1,3-Propanedione | 20 | — | 10 |
| 2-Pyrrolidinone | 10 | 5 | 2.5 |
| Tetramethylene Sulfone | 10 | 5 | 2.5 |
| Triethylene Glycol | 10 | — | 5 |
| Valerolactam | 5 | 2.5 | 1.25 |

Example 7

Testing Glycols and Tween® 80 in Extraction

In previous experiments, DNA extracted from blood-stained cards with 50% formamide was successfully amplified. Also, Tween® 80, diethylene glycol, and 1, 3 propanediol showed encouraging results. In this experiment, eight 3 mm bloodstained S&S 903 disks were extracted in 100 μL of solution (Table 5) using standard protocols. A two-fold dilution series was used in a standard PCR reaction.

All reactions with the glycols failed. The buffered formamide solutions results are similar to previous results, although the solution containing 5.94% formamide produced results that were not consistent. The solutions containing 10% or 5% Tween® 80 produced good results.

TABLE 5

Testing Tween® 80 and Glycols in Extraction

| Solution | Detectable PCR Dilution Range |
|---|---|
| 95% Formamide, 100 mM Tris pH 8.3 | $2^{-4}$–$2^{-8}$ |
| 47.5% Formamide, 100 mM Tris pH 8.3 | $2^{-2}$–$2^{-11}$ |
| 23.75% Formamide, 100 mM Tris pH 8.3 | All failed |
| 11.88% Formamide, 100 mM Tris pH 8.3 | $2^{-1}$–$2^{-2}$ |
| 5.94% Formamide, 100 mM Tris pH 8.3 | $2^{-1}$–$2^{-5}$ |
| 20% Tween ® 80 | All failed |
| 10% Tween ®80 | $2^{-1}$–$2^{-5}$ |
| 5% Tween ®80 | $2^{-1}$–$2^{-7}$ |
| 40% Diethylene Glycol | All failed |
| 20% Diethylene Glycol | All failed |
| 40% 1,3 Propanediol | All failed |
| 20% 1,3 Propanediol | All failed |

Example 8

Combining Formamide and Tween® 80 in Extraction

The solutions that produced the best PCR targets over the dilution range were (1) 11.9% formamide, 50 mM Tris pH 8.3 and (2) 5.9% formamide, 50 mM Tris pH 8.3. The addition of Tween® 80 seemed to slightly decrease the effectiveness of the extraction solution.

TABLE 6

Formamide and Tween ®80 Combinations

Extraction Solution
95% Formamide, 50 mM Tris pH 8.3
47.5% Formamide, 50 mM Tris pH 8.3
23.8% Formamide, 50 mM Tris pH 8.3
11.9% Formamide, 50 mM Tris pH 8.3
5.9% Formamide, 50 mM Tris pH 8.3
20% Tween ®80
10% Tween ®80
5% Tween ®80
20% Tween ®80, 50 mM Tris pH 8.3
10% Tween ®80, 50 mM Tris pH 8.3
5% Tween ®80, 50 mM Tris pH 8.3
47.5% Formamide, 50 mM Tris pH 8.3, 10% Tween ®80
23.8% Formamide, 50 mM Tris pH 8.3, 10% Tween ®80
11.9% Formamide, 50 mM Tris pH 8.3, 10% Tween ®80
5.9% Formamide, 50 mM Tris pH 8.3, 10% Tween ®80
47.5% Formamide, 50 mM Tris pH 8.3, 5% Tween ®80
23.8% Formamide, 50 mM Tris pH 8.3, 5% Tween ®80
11.9% Formamide, 50 mM Tris pH 8.3, 5% Tween ®80
5.9% Formamide, 50 mM Tris pH 8.3, 5% Tween ®80
2.5% Chelex, 10% Tween ®80
10% Tween ®80, 1 mM EDTA Example 9

Testing Citrate as Inhibitor of DNA Degradation During Heating

In an attempt to improve the extraction solution, citrate was tested as an inhibitor of DNA degradation during the heating process. Eight 3 mm bloodstained S&S 903 disks were extracted in 150 μL of the solutions listed in table 7 using standard protocols. The supernatants were diluted by adding 450 μL water. A two-fold dilution series was used as a target (one-half the volume of the reaction) in standard PCR reactions. The reactions were qualitatively graded (−poor to ++++very good) for performance as listed in Table 7. Citrate performed very well in the extraction and PCR.

However, all reactions that contained 5 mM citrate (the highest final concentration) were partially inhibited.

TABLE 7

Citrate in Extraction Buffer

| Solution | PCR performance (Citrate concentration) | | | |
|---|---|---|---|---|
| | None | 10 mM | 20 mM | 40 mM |
| Water | − | − | + | ++ |
| 50 mM Tris pH 8.3 | + | ++ | +++ | |
| 50 mM Tris pH 8.3, 6% formamide | ++ | +++ | +++ | |
| 50 mM Tris pH 8.3, 12% formamide | ++ | +++ | ++++ | ++++ |

Example 10

Determining Optimum Number and Size of Disks and Volume of Extraction

The next evaluation was designed to determine the number and size of disks and the volume of extraction solution to use. Disks were extracted in 10% formamide, 50 mM Tris pH 8.3, and 20 mM citrate as described in Table 8 using standard procedures. A two-fold dilution series was used as target (one-half the volume of the reaction) in standard PCR reactions.

The 6 mm disks were too big to be used in a 96-well plate format. They do not fall freely to the bottom of the well. Extraction of DNA from a single 3 mm or 3.2 mm disk produced less product than extractions with more or larger punches. A single 4.7 mm punch produced amplified product under all conditions tested. A single 4.7 mm punch extracted in approximately 50 μL is likely the best system.

TABLE 8

Testing Disk Number, Size and Extraction Volume

| Disk Number and Size | Extraction Volume |
|---|---|
| 8 × 3 mm | 100 |
| 4 × 3 mm | 100 |
| 2 × 3 mm | 100 |
| 1 × 3 mm | 100 |
| 1 × 3.2 mm | 100 |
| 1 × 4.7 mm | 100 |
| 2 × 4.7 mm | 100 |
| 1 × 6 mm | 100 |
| 2 × 6 mm | 100 |
| 1 × 3.2 mm | 80 |
| 1 × 3.2 mm | 60 |
| 1 × 3.2 mm | 40 |
| 1 × 3.2 mm | 20 |
| 1 × 4.7 mm | 80 |
| 1 × 4.7 mm | 60 |
| 1 × 4.7 mm | 40 |
| 1 × 4.7 mm | 20 |

Example 11

Testing Extraction on FTA™ Paper with Tween®80

The next experiment was designed to test the optimized extraction buffer system on FTA paper. Since Tween®80 had previously been shown to reverse PCR inhibition due to SDS, a component of FTA™ paper, it was included in some PCR reactions. Bloodstained disks (one 4.7 mm S&S 903 or FTA™) were extracted in 50 μL of 50 mM Tris pH 8.3, 20 mM citrate, and 10% formamide using standard protocols. Then the supernatants were diluted three-fold in water, mixed, and centrifuged for 10 minutes at 3850 rpm. These solutions are defined as neat. The results of this experiment are shown in Table 9. These supernatants were diluted two-fold in water. This supernatant was serially diluted with water or Tween®80 solution and these solutions served as targets (5 μL in 10 μL reaction) in standard PCR.

This experiment produced good results with FTA™ paper provided that the PCR reaction included Tween®80. The inhibitors from the FTA™ paper do not completely inhibit PCR in the absence of Tween®80 with the target dilution of $2^{-4}$. Tween®80 at 1% produced better amplification than at a concentration of 0.2%. However, there might be some inhibition of amplification in extracts from S&S 903 paper at the higher Tween®80 concentration.

TABLE 9

Tween ®80 in Extraction Solution

| | PCR Result at Final Target Dilution | | |
|---|---|---|---|
| Final Tween ®80% | $2^{-2}$ | $2^{-3}$ | $2^{-4}$ |
| S&S 903 | | | |
| 0.0 | | ++ | ++ |
| 0.2 | NA | | ++ |
| 1.0 | NA | | ++ |
| FTA ™ | | | |
| 0.0 | − | − | + |
| 0.2 | NA | + | + |
| 1.0 | NA | ++ | ++ |

Example 12

Testing Effect of pH on Extraction Efficiency

The next experiment was designed to test the effect of varied pH on the extraction process. Bloodstained S&S 903 disks (one 4.7 mm) were extracted in 50 μL of 30 mM Tris (combinations of Tris base and Tris HCl indicated in Table 10), 20 mM citrate, and 10% formamide. The disks were incubated at room temperature for 10 minutes with agitation, incubated at 95° C. for 10 minutes, and diluted three-fold to a final Tris concentration of 20 mM. This dilution either normalized the Tris to a mixture of 50:50 Tris base:Tris HCl (normalized) or maintained the ratio in the extraction buffer (not normalized). Following dilution, the plates were centrifuged for 10 minutes at 3850 rpm and the supernatants were collected. All extractions and reactions were performed in duplicate. Two-fold serial dilutions of the solutions served as targets for amplification.

The extraction buffer functions well over a wide pH range. All dilutions amplified except those at $2^{-1}$ for 100% Tris HCl. Extractions at 20–40% Tris base generated the best amplification, although in 20% Tris base, the amplification was slightly weaker. Little difference was observed between amplifications from extracts that were normalized versus those that were not normalized. it is clear that pH below 8.3 has advantages. The PCR buffer used in these experiments has a pH between 7.8 and 7.9. This pH of extraction solution produced the best results.

TABLE 10

Test Extraction Buffer pH

| % Tris Base | pH of Solution |
|---|---|
| 100 | 10.27 |
| 80 | 8.73 |
| 60 | 8.31 |
| 50 | 8.11 |
| 40 | 7.94 |
| 20 | 7.51 |
| 0 | 4.62 |

Example 13

Testing the Extraction System in Multiplex PCR

As a final test of the extraction buffer, a multiplex PCR reaction was tested. DNA was extracted from one 4.7 mm disk (either FTA or S&S 903) in 50 µL of extraction buffer (10% formamide, 50 mM Tris pH 8.3, 20 mM citrate) using standard protocols. These solutions were used as targets in Profiler+genotyping reactions (3 µL reactions with 1 µL target). The extracted DNA solutions were diluted in Tween®80 solutions to give a final concentration of 1/12 or 1/24 target and 0, 0.13 and 0.67% Tween®80 in the PCR reaction. The Perkin Elmer buffer or our production PCR buffer supplemented with dNTPs at a final concentration in the reaction of 133 µM was used.

Only the control sample amplified in the Perkin Elmer buffer. The FTA and S&S 903 samples all failed. Surprisingly, all samples in production buffer amplified well. This is likely due to the pH resulting from combinations of PCR buffer and extraction buffer. Production PCR buffer seems more compatible than Perkin Elmer buffer using these extracts as a target. The more dilute samples (1/24) produce markedly lower signal.

Example 14

Testing the Extraction System with Alternative Dried Specimens

Replicate samples of dried buccal smears and semen were extracted in accordance with the above process. PCR amplification was performed on the DNA and the results analyzed. It was found that the PCR amplification was also successful for dried buccal smears and semen.

Conclusions:

A simple extraction technique for releasing DNA from bloodstained S&S 903 and FTA™ cards has been described. This technique uses single paper disks and can be performed in a single tube with a simple extraction solution (10% formamide, 50 mM Tris pH 7.8, 20 mM citrate). Tween®80 at 1% concentration improves amplification of extracts from FTA paper. The system works well for PCR amplification and has the potential to be used for genotyping in multiplex reactions.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A method for extracting DNA from a biological sample dried on a solid support which comprises:
    (a) contacting the biological sample with a DNA extraction composition comprising:
        (1) 5% to 90% formamide;
        (2) 5 mM to 60 mM citrate; and
        (3) 1 mM to 300 mM buffer, pH 6.0 to 8.8;
    (b) incubating the mixture for 0.5 to 60 minutes at 4° to 60° C.;
    (c) incubating the mixture for 0.5 to. 60 minutes at 45° to 100° C.; and
    (d) isolating a supernatant containing extracted DNA.

2. The method of claim 1, wherein the DNA extraction composition further comprises 0.1% to 50% non-ionic detergent.

3. The method of claim 1, wherein the biological sample is selected from the group consisting of buccal smears, semen and blood.

4. The method of claim 1, wherein said extraction is carried out in a single tube.

5. The method of claim 1, which comprises:
    (a) contacting the biological sample with a DNA extraction composition comprising:
        (1) 5% to 50% formamide;
        (2) 10 mM to 40 mM citrate; and
        (3) 10 mM to 150 mM buffer, pH 7.5 to 8.3;
    (b) incubating the mixture for 5 to 20 minutes at 10° C. to 45° C.;
    (c) incubating the mixture for 5 to 20 minutes at 55° C. to 100° C.; and
    (d) isolating a supernatant containing extracted DNA.

6. The method of claim 1 which comprises:
    (a) contacting the biological sample with of a DNA extraction composition comprising:
        (1) 10% formamide;
        (2) 20 mM to 40 mM citrate; and
        (3) 50 mM buffer, pH 7.8;
    (b) incubating the mixture for 10 minutes at room temperature;
    (c) incubating the mixture for 10 minutes at 95° C.; and
    (d) isolating a supernatant containing extracted DNA.

7. The method of claim 3, wherein the biological sample is dried on a cellulosic material.

8. The method of claim 5, wherein the DNA extraction composition further comprises 0.5% to 10% non-ionic detergent.

9. The method of claim 5, wherein the buffer is Tris.

10. The method of claim 5, wherein said biological sample is selected from the group consisting of buccal smears, semen and blood.

11. The method of claim 6, wherein the DNA extraction composition further comprises 1% non-ionic detergent.

12. The method of claim 6, wherein the buffer is Tris.

13. The method of claim 6, wherein said biological sample is selected from the group consisting of buccal smears, semen and blood.

14. The method of claim 7, wherein 1 to 20 disks of 1 mm to 5 mm of said cellulosic material is used.

15. The method of claim 8, wherein the non-ionic detergent is polyoxyethylene sorbitan monooleate.

16. The method of claim 8, wherein said biological sample is selected from the group consisting of buccal smears, semen and blood.

17. The method of claim 11, wherein the non-ionic detergent is polyoxyethylene sorbitan monooleate.

18. The method of claim 11, wherein said biological sample is selected from the group consisting of buccal smears, semen and blood.

19. The method of claim 14, wherein 20 µL to 300 µL of DNA extraction composition is contacted with said cellulosic material.

* * * * *